United States Patent
Prosser

(10) Patent No.: US 7,591,852 B2
(45) Date of Patent: Sep. 22, 2009

(54) VERTEBRAL BODY REPLACEMENT CAGE ASSEMBLY

(75) Inventor: Michael Prosser, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 10/579,661

(22) PCT Filed: Dec. 2, 2004

(86) PCT No.: PCT/US2004/040244

§ 371 (c)(1),
(2), (4) Date: May 17, 2006

(87) PCT Pub. No.: WO2005/055869

PCT Pub. Date: Jun. 23, 2005

(65) Prior Publication Data

US 2007/0100452 A1  May 3, 2007

Related U.S. Application Data

(60) Provisional application No. 60/526,241, filed on Dec. 2, 2003.

(51) Int. Cl.
*A61F 2/44* (2006.01)
(52) U.S. Cl. .................. 623/17.16; 623/17.11
(58) Field of Classification Search ... 623/17.11–17.16; 606/61, 246, 279
See application file for complete search history.

(56) References Cited

U.S. PATENT DOCUMENTS

| | | | | |
|---|---|---|---|---|
| 5,192,327 A | * | 3/1993 | Brantigan | 623/17.11 |
| 6,159,211 A | * | 12/2000 | Boriani et al. | 606/61 |
| 7,309,358 B2 | * | 12/2007 | Berry et al. | 623/17.16 |
| 2004/0073314 A1 | * | 4/2004 | White et al. | 623/17.15 |
| 2005/0060034 A1 | * | 3/2005 | Berry et al. | 623/17.11 |

* cited by examiner

*Primary Examiner*—Thomas C Barrett
*Assistant Examiner*—Andrew Yang
(74) *Attorney, Agent, or Firm*—Mintz, Levin, Cohn, Ferris, Glovsky and Popeo PC

(57) ABSTRACT

A cage assembly adapted to be implanted in a spinal column for treating degenerative or ruptured discs and replacing damaged vertebral bodies. The assembly includes one or more rigid cages formed in an annular configuration and having opposed upper and lower perimeter surfaces, an annular side wall extending between said surfaces, a transverse inner wall extending across said cage, a plurality of raised ridges projecting outwardly from each of said perimeter surfaces for engaging the spinal column and securing the assembly therein. Apertures are provided in the side wall for use in positioning said cage in the spinal column and a pair of aligned openings extend axially through the cage for packing the cage with bone graft material. At least one spacing element having the same annular configuration as the cages can be provided to effect the stacked attachment of one cage with another in rigid axial alignment.

25 Claims, 9 Drawing Sheets

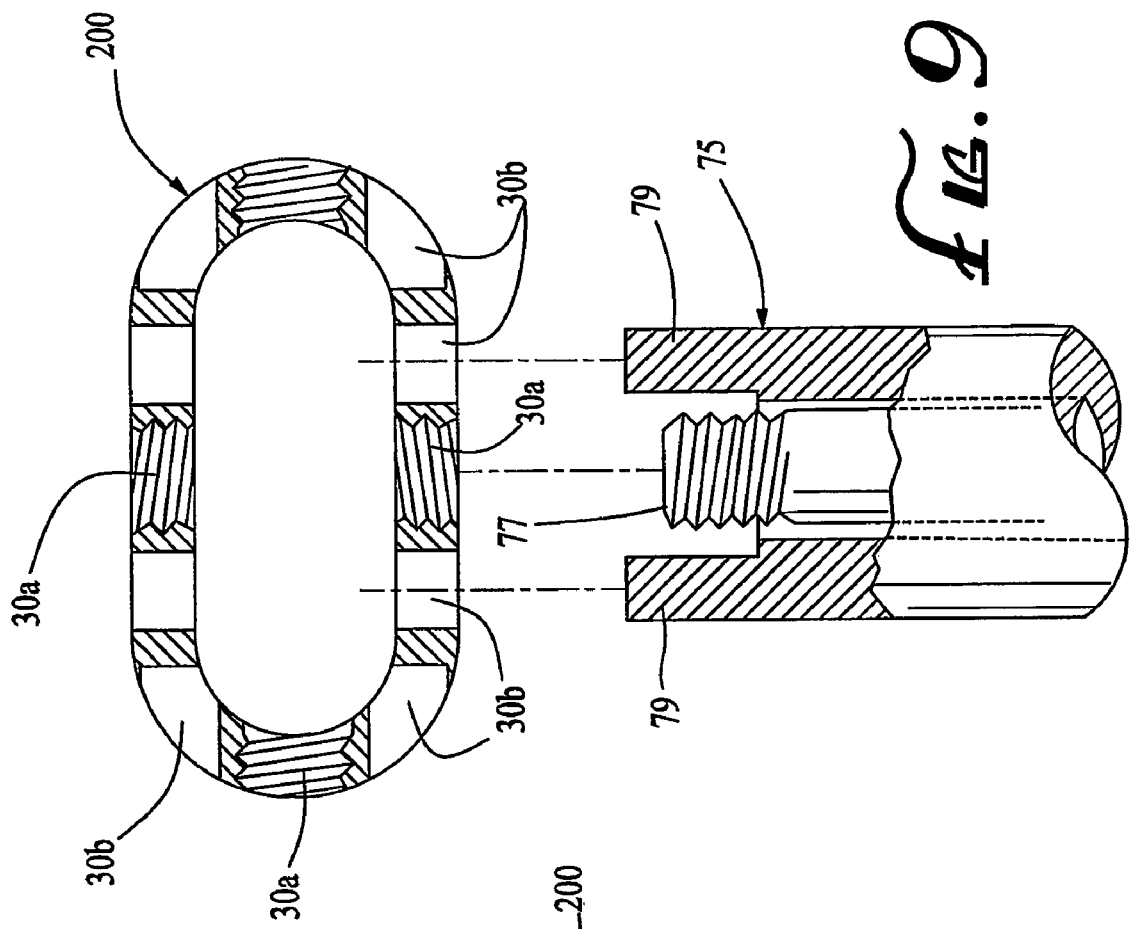
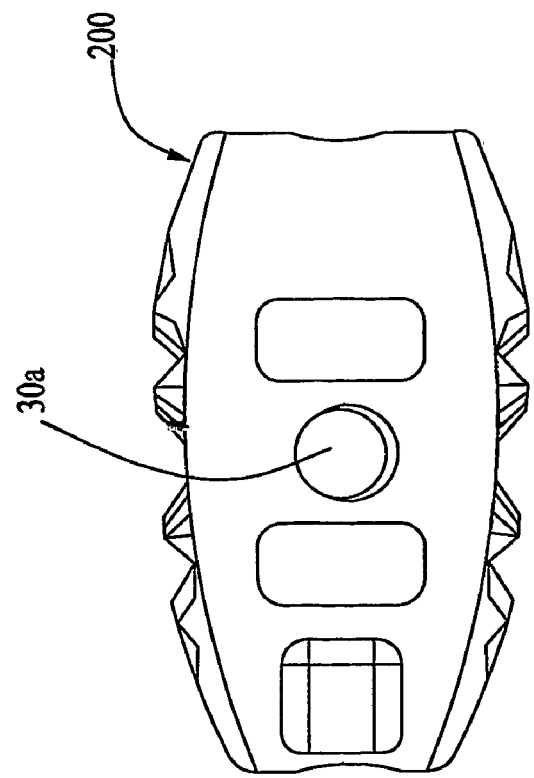

VERTEBRAL BODY REPLACEMENT CAGE ASSEMBLY

This application is a United States national phase application based on International Application No. PCT/US2004/040244, filed Dec. 2, 2004 and claims priority to U.S. Provisional Patent Application No. 60/526,241, filed Dec. 2, 2003. The disclosures of these applications are incorporated herein by reference in their entirety.

BACKGROUND OF THE INVENTION

The present invention relates to prosthetic devices adapted to be implanted between the vertebrae for treating degenerative or ruptured discs and for replacing damaged vertebral bodies. More particularly, the invention comprises a rigid vertebral body replacement cage which is annular in configuration and shaped for its particular application. The cages can be formed in a half-moon shape to be used in the center of the vertebral body, a modified kidney-shape to be used in the anterior portion of the vertebral body or of a smaller oval configuration for lateral applications on the sides of the vertebral body. The cages are configured to be used singularly or in stacked combination to replace a damaged disc and/or vertebrae and can also be secured inside the fibrous disc column connecting adjoining vertebrae to provide the necessary support in the spinal column.

While vertebral body replacement devices have been in use for several years, efforts have been ongoing to improve them. As a result of their configuration, the vertebral body replacement cages of the present invention are not only particularly well suited for their intended purpose, they are very versatile in their applications, easily placed into proper position during the operative procedure, whether used individually or in a stacked configuration and, when used in a stacked configuration, are far more easily joined together in a secure stack of desired length than those cages heretofore available. The result is a substantial improvement in vertebral body replacement devices.

SUMMARY OF THE INVENTION

Briefly, the present invention is directed to a vertebral body replacement cage assembly adapted to be implanted between the vertebrae for treating degenerative or ruptured discs and for replacing damaged vertebral bodies. The assembly comprises one or more rigid cages that are configured to be used singularly or in a stacked combination to fill differently sized evacuated spaces. Each cage is formed of a biologically accepted inert material, is of an annular configuration and is particularly shaped and sized for its particular application. The assembly also includes one or more spacing elements for joining together two or more cages in a stacked configuration to provide the assembly with its desired axial length.

Each cage in the assembly of the present invention defines opposed upper and lower perimeter surfaces, an annular side wall extending between said surfaces and, for several applications, a transverse inner wall. The upper and lower perimeter surfaces each define a plurality of outwardly projecting spaced ridges thereon for biting and gripping into the vertebral end plates. The annular side wall of the cage has a plurality of tool engaging openings therein to facilitate insertion of the cage in any desired angular orientation and cooperates with the transverse wall to define a pair of openings extending axially through the cage which are adapted to be packed with bone graft material to expedite the fusion of the cage in the spinal column. A plurality of indexing apertures are provided in the perimeter surfaces of the cage for receiving a corresponding plurality of indexing pins on a spacing element for stacked applications.

The spacing elements in the cage assembly preferably have the same general annular shape as the cages with which they are used but are shorter in axial dimension. The spacing elements each define the above-identified indexing pins and two pair of opposed outwardly projecting locking tabs that are adapted to engage wall portions of a pair of adjacent cages when the indexing pins on the spacing element are inserted into the indexing apertures on a pair of adjacent cages, thereby effecting an operative securement of the spacing member between a pair of cages and a rigid cage assembly of a desired axial length corresponding to the length of the evacuated area. Thus, the present invention provides a very versatile assembly for replacing damaged discs and/or vertebrae which can also be secured inside the fibrous disc column connecting adjoining vertebrae to provide the spinal column with the necessary support.

DESCRIPTION OF THE PREFERRED EMBODIMENTS IN THE DRAWINGS

FIG. 8 is a side view of the oval-shaped cage shown in FIG. 6.

FIG. 9 is a partial sectional view as seen from above of the oval-shaped cage shown in FIG. 6 proximate the extended end of an insertion tool used therewith.

DETAILED DESCRIPTION OF THE PREFERRED EMBODIMENTS

Figure 5:
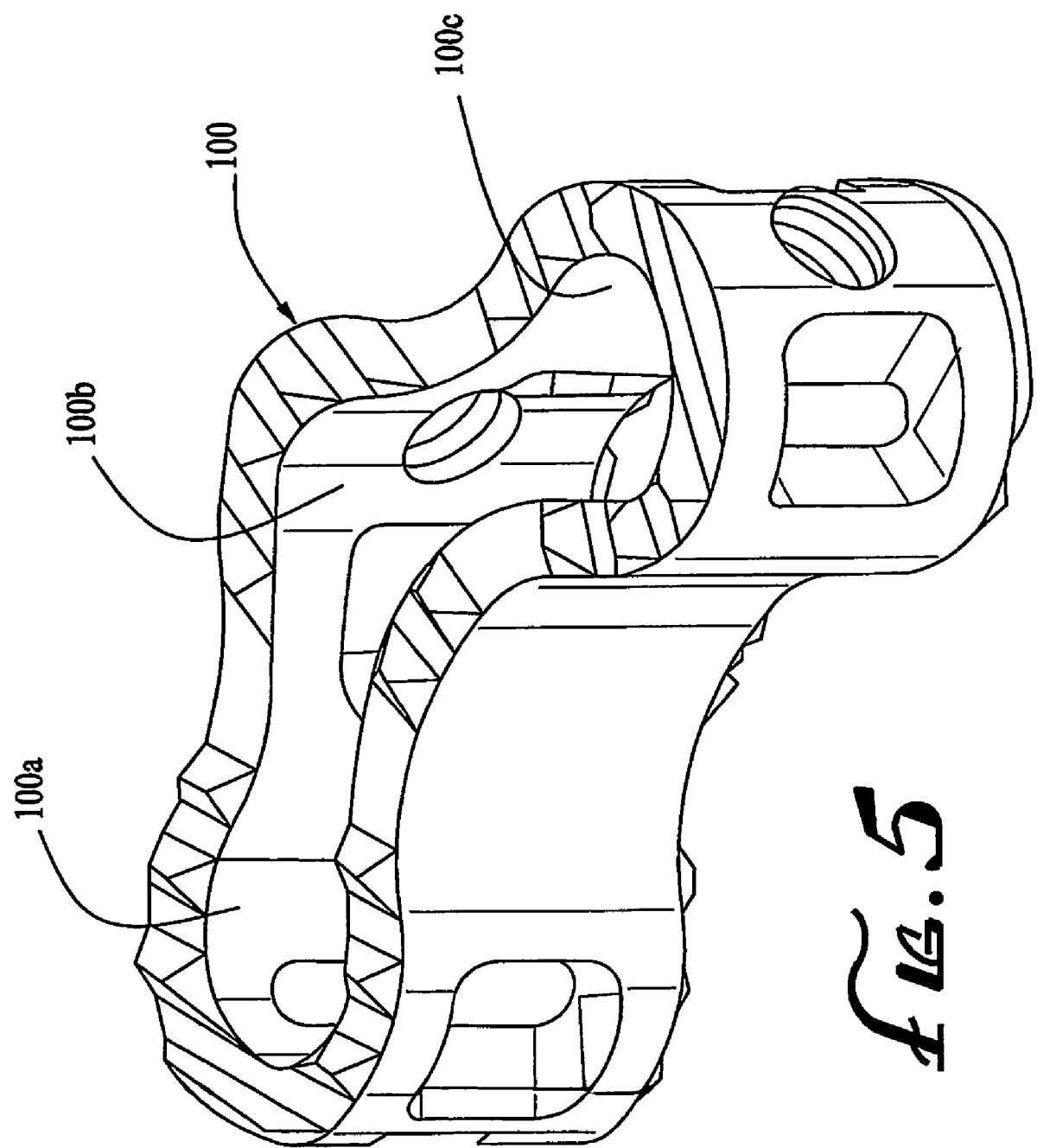
FIG. 5 is a perspective view of a second embodiment of a vertebral body replacement cage of the present invention wherein the cage is of a modified kidney-shape.
Figure 6:
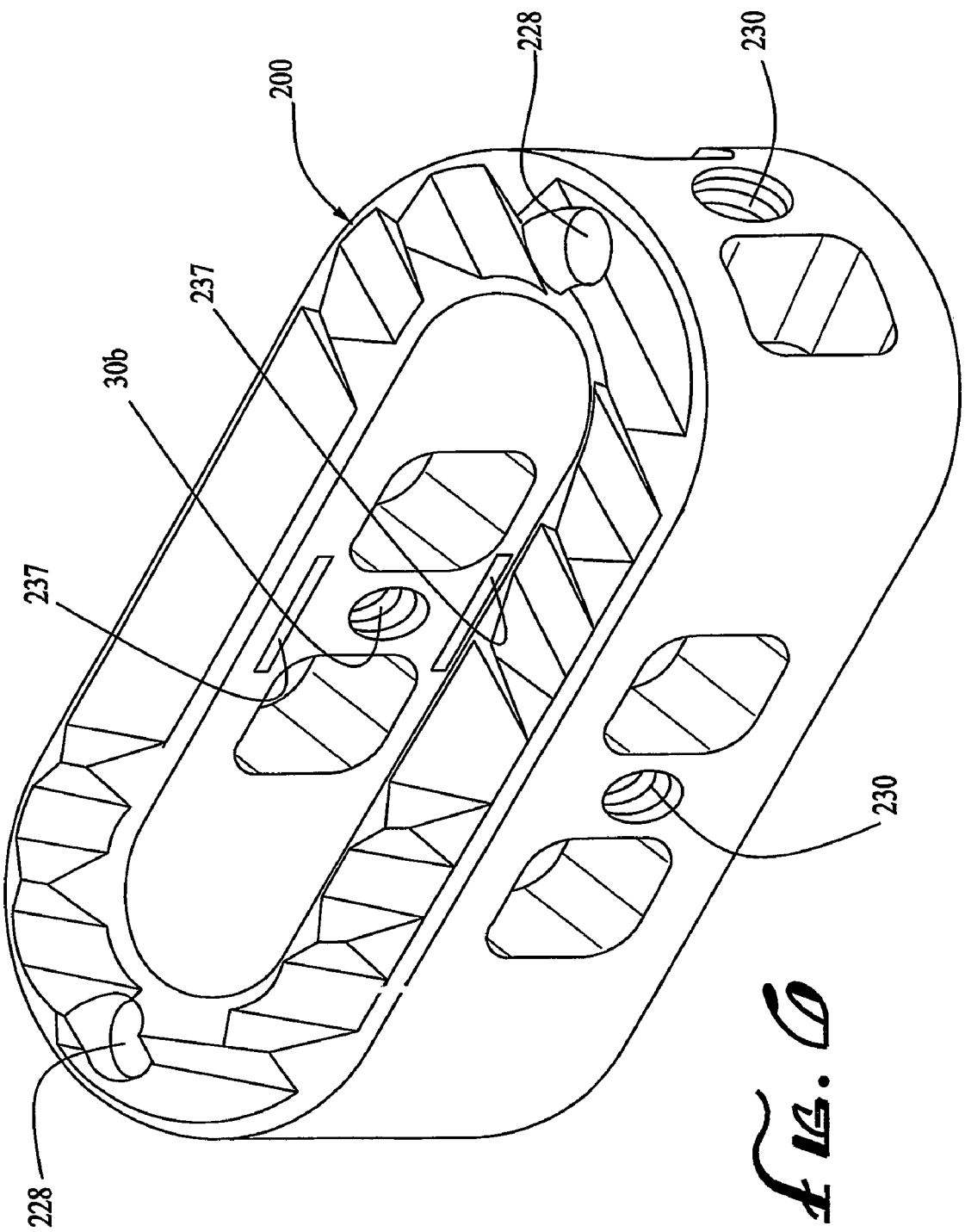
FIG. 6 is a perspective view of a second embodiment of a vertebral body replacement cage of the present invention wherein the cage is of a modified oval shape.
Figure 10:
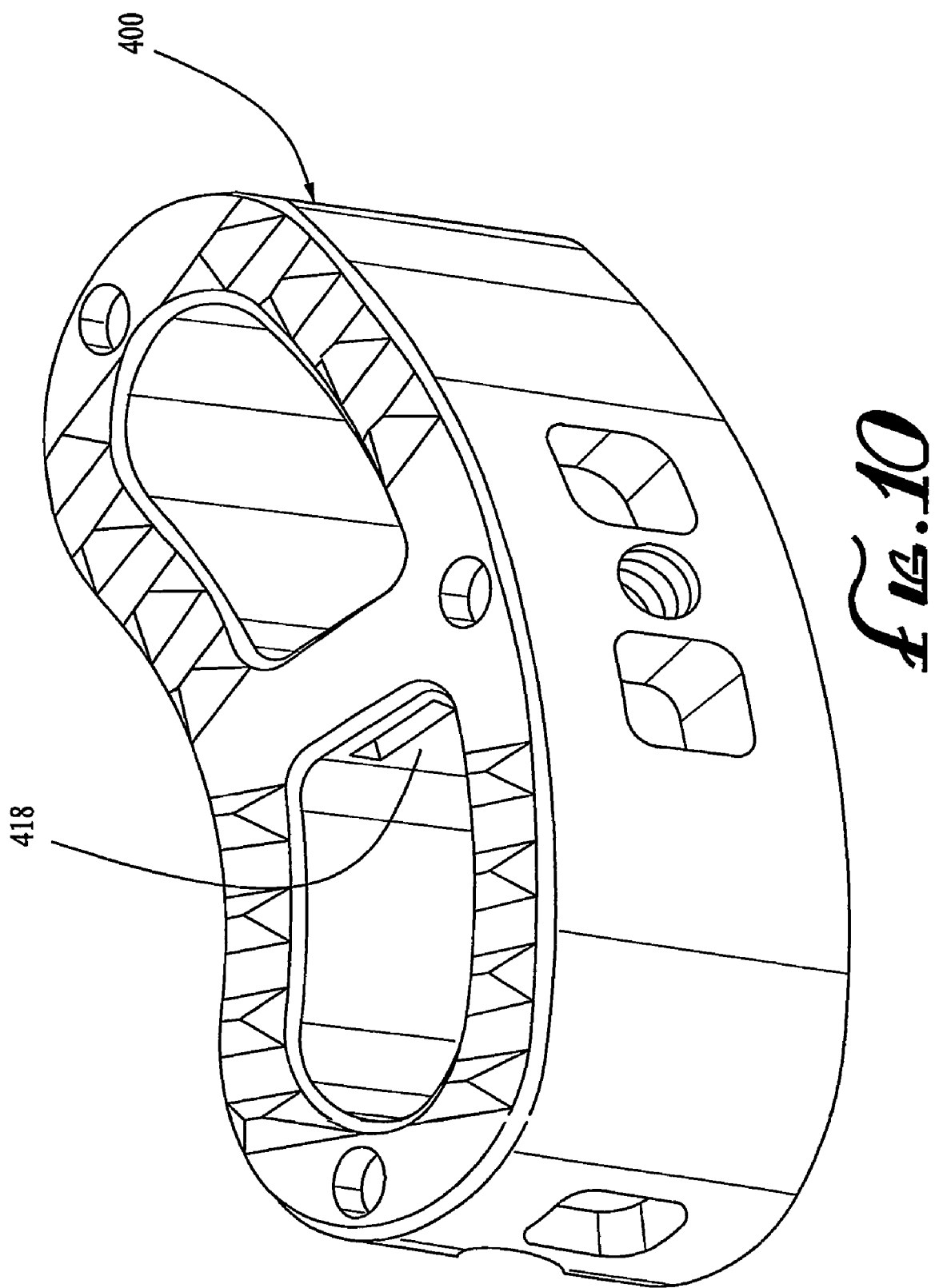
FIG. 10 is a perspective view of a kidney-shaped vertebral body replacement cage of the present invention.

Referring now in detail to the drawings, the vertebral replacement cage of the present invention is of a rigid construction and preferably provided in three basic shapes with each shape being provided in several different sizes (horizontally and vertically) to fill differently sized evacuated spaces in differently sized individuals. The cage is annular in configuration and in the embodiment shown in FIGS. 1 and 2-4, is "half-moon"-shaped for use in the center of the vertebral body. Three other shapes of the replacement cage are illustrated in FIGS. 5, 6 and 10 and will be discussed later herein.

Cage 10, illustrated in FIGS. 1-4, is preferably constructed of commercially pure titanium, a titanium alloy or of a radiolucent material such as polyetherketoneketone (PEKK), although it could be formed of other biologically acceptable inert materials that would provide the cage 10 with a rigid structure. Cage 10 defines an upper surface 12, an opposed lower surface 14, an annular side wall 16 and a transverse inner wall 18. While only the upper surface 12 of the cage is visible in the drawings, lower surface 14 is preferably identical in configuration. Accordingly, the following description generally will be with references only to the upper surface 12. It is to be understood, however, that the description is equally applicable to the lower surface 14 of the cage.

Figure 1:
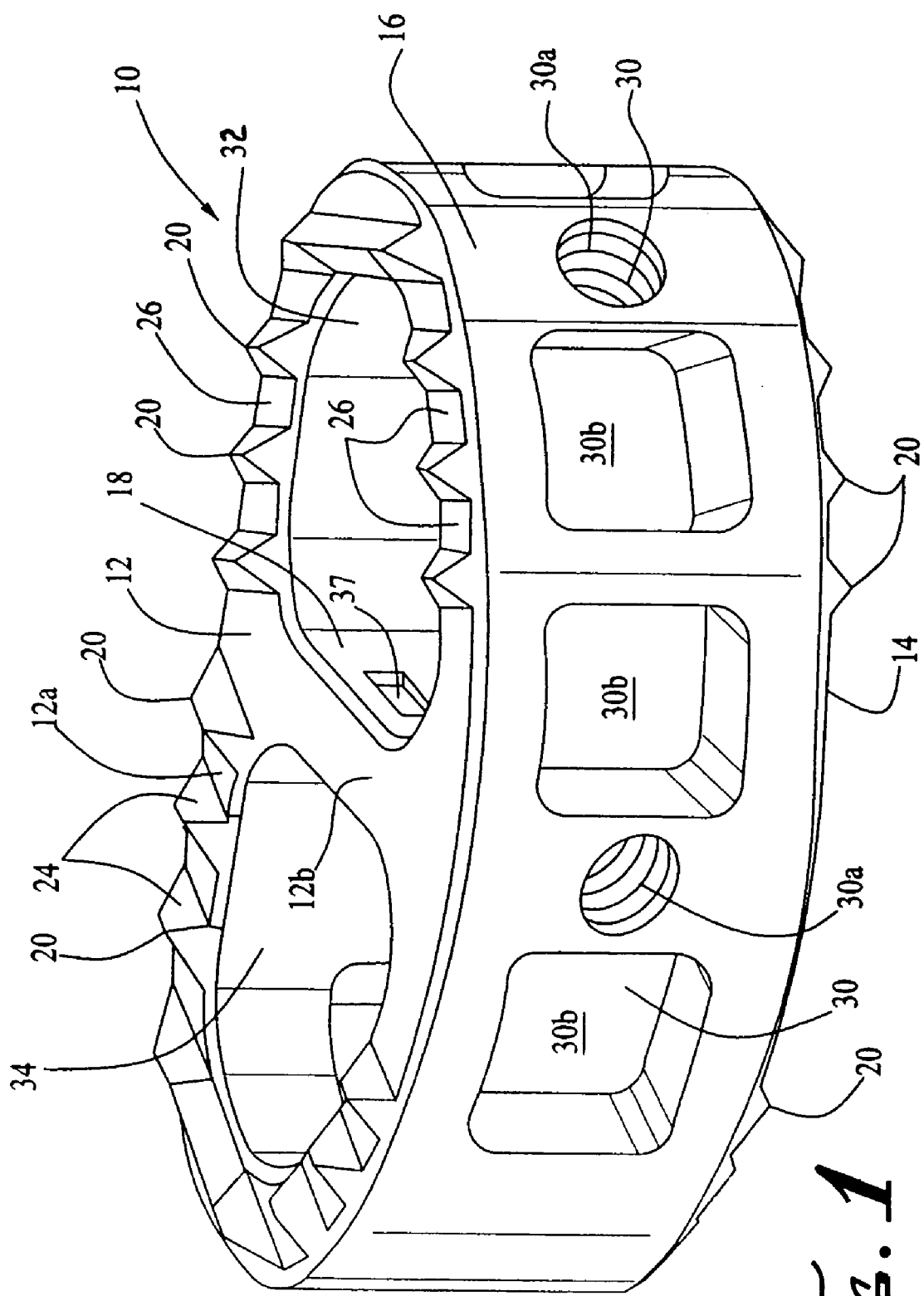
FIG. 1 is a perspective view of a first embodiment of the vertebral body replacement cage of the present invention.

Surface 12 of cage 10 defines a perimeter portion 12a and a transverse portion 12b. A plurality of outwardly projecting sharp raised ridges 20 are formed in the perimeter portion 12a of surface 12 for biting into and gripping the vertebral end plates (not shown). The ridges 20 preferably are disposed at slightly offset angles with respect to each other or, alternatively with respect to the ridges on different portions of the cage, to reduce the possibility of the ridges sliding in any direction along the end plates and to prevent rotation of the cage on the end plate. For example, as shown in FIG. 1, the ridges on one side of the transverse wall 18 are all in parallel alignment, but misaligned with the ridges 20 on the other side of wall 18. All of the ridges 20 taper outwardly from its relatively sharp edge along inclined walls 24 into enlarged open areas 26 between the individual ridges.

Figure 2:
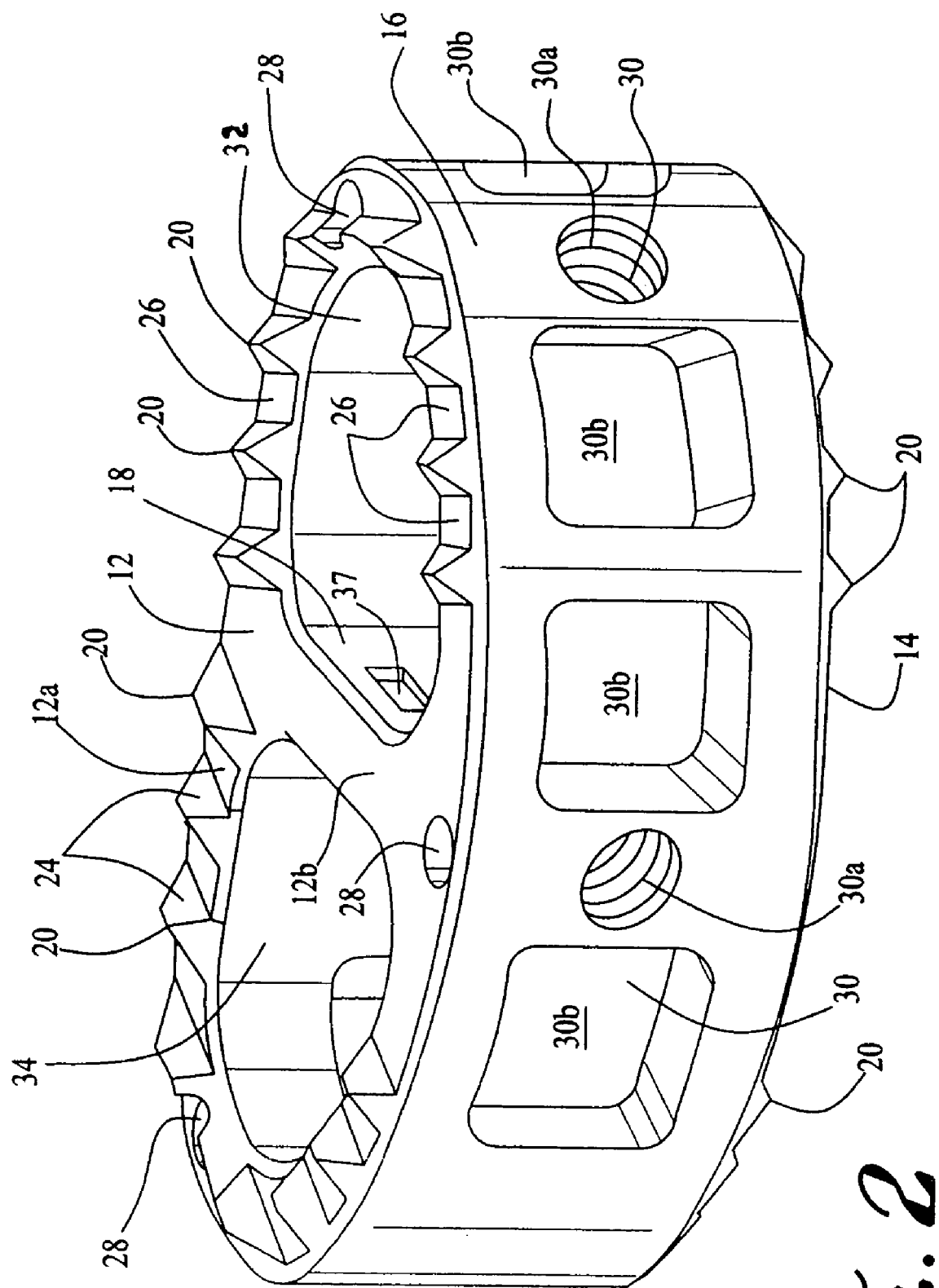
FIG. 2 is a perspective view of a first embodiment of the vertebral body replacement cage of the present invention which has been modified for stacked applications.

For stacked applications (see FIGS. 2-4), a plurality of indexing apertures 28 are also provided in the outer surfaces 12 and 14 of cage 10. Preferably, three such apertures 28 are provided in each of the opposed surfaces, one aperture being disposed in each surface proximate each end of the cage and the third aperture at the juncture of the perimeter and transverse surfaces as seen in FIG. 2.

A plurality of tool engaging openings 30 are disposed in the side wall 16 of the cage. Openings 30 can be threaded or otherwise configured to receive a conventional insertion tool (not shown) and are preferably spaced about the cage 10 so as to provide one such opening 30 at each of the opposed ends of the cage and a plurality of openings 30 along the anterior and posterior sides of the cage. In the preferred configuration illustrated in FIGS. 1-4, the openings 30 are arranged in groups of three to accommodate the insertion tool illustrated in FIG. 9. In each opening or aperture grouping, a threaded circular aperture 30a is disposed between a pair of unthreaded generally rectangular openings 30b to accommodate the insertion tool 75 which includes a rotatable threaded shank 77 disposed between a pair of prongs 79 so that the tool can grip the cage for insertion and manipulation as suggested in FIG. 9. As seen, for example, in FIGS. 1 and 2, the groupings of openings 30 are provided at each end of the cage 10 at the interior side of the cage so as to be centered thereon and at a 45 degree inclination with respect to the central axis of transverse inner wall 18. So positioned, the tool can grip the cage at either end thereof and at 90 and 45 degree angles with respect to the cage ends. Only one aperture grouping at a 45 degree inclination is needed in view of the symmetry of the cage. As a result of such a configuration convenient access is always provided to at least one of the groupings to facilitate insertion of the cage in any desired angular orientation. So configured, the cage 10 also defines a pair of axially aligned openings 32 and 34 extending therethrough which can easily be packed with bone graft material to expedite the fusion of the cage in the spinal column.

For those applications that require a prosthesis of greater length than can be effectively provided by a single vertebral body replacement cage and to provide greater flexibility in cage length (vertical elevation) without having to provide a corresponding inventory of cages, cage 10 is adapted for use with one or more spacing elements 38 to provide a rigid stack of cages. To provide such versatility, cage 10 includes two pair of opposed tab receiving slots 37 in opposite sides of the transverse inner wall 18 proximate the upper and lower surfaces of wall 18. Slots 37 are used in the securement of one or more spacing elements 38 to provide such a stack of cages as will be described.

Figure 3:
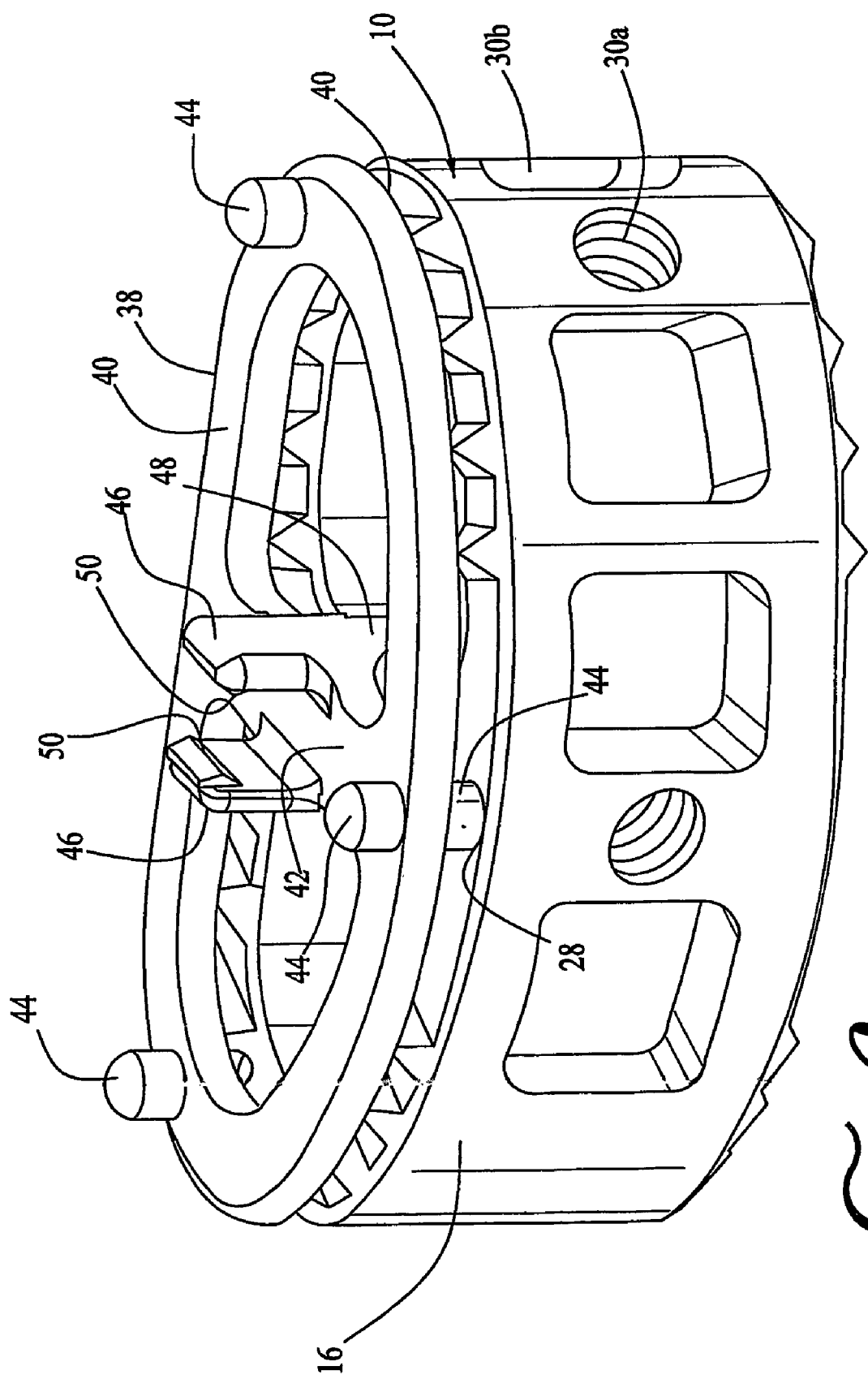
FIG. 3 is a perspective view of the cage shown in FIG. 1 with a spacing element attached thereto.
Figure 4:
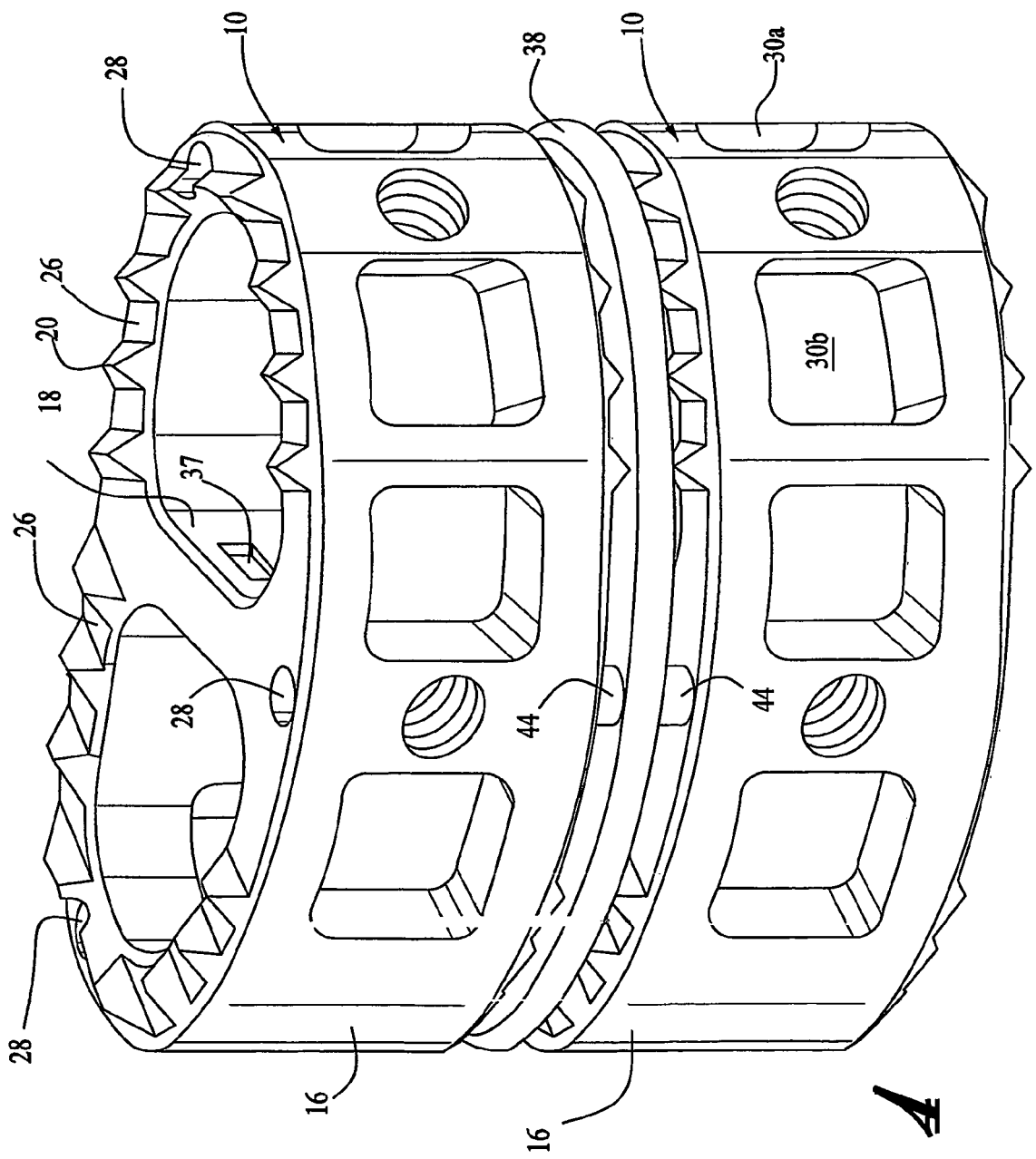
FIG. 4 is a perspective view of a pair of the first embodiment of the replacement cages of the present invention secured together by a spacing element in a stacked configuration in accordance with the present invention.

FIG. 3 illustrates the securement of a cage 10 to a spacing element 38 to form a secure stack of two such cages as seen in FIG. 4. Spacing element 38 is preferably constructed of titanium and is of a substantially identical annular configuration as the cages 10 with which it is being used. Spacing element 38 defines opposed identical upper and lower perimeter surfaces 40 and transverse surfaces 42 extending therebetween. Again, only the upper surfaces are seen in the drawings. Unlike the perimeter surfaces of cage 10, the perimeter surfaces of element 38 are preferably flat. A plurality of indexing pins 44 project from both the upper and lower surfaces 40 at spaced locations thereon corresponding to the locations of the indexing apertures 28 in cages 10. In addition, spacing element 38 is provided with two pair of identical spaced locking tabs 46 and 48 extending in opposed axial directions as seen in FIG. 3. Each pair of tabs defines a pair of tapered transversely extending projections 50 adjacent the extended tab ends which are adapted to be received in the transversely extending tab slots 37 formed in the opposed sides of the interior transverse wall 18 of cage 10.

As a result of the resilient nature of the locking tabs 46 and 48, the spacing element 38 is easily secured to one of cages 10 by merely aligning the indexing pins 44 on element 38 with the indexing apertures 28 in the cage and pressing the pins into the apertures. The resilient locking tabs 46 or 48 will extend about the opposite sides of the inner transverse wall 18 of the cage and the projections 50 adjacent the ends of the tabs will snap into the slots 36 in the cage wall 18, rigidly securing the spacing element 38 to the cage 10. A second cage of the same or different vertical elevation can then easily be inserted over and locked to the opposite side of the spacing element 38 as shown in FIG. 4 to provide the desired overall length of the cage assembly. If needed, a second spacing element and an additional cage could be added to the stack to increase further the overall length of the cage assembly.

As noted earlier, different shapes of cage 10 are provided for different applications. For example, the cage would preferably be formed in an annular somewhat kidney-shaped configuration such as that shown in FIG. 5 for use in the anterior portion of the vertebral body. Such a configuration is referred to herein as a modified kidney-shaped configuration and is formed by three circular segments 100a, 100b and 100c joined together such that segments 100a and 100c lie on a common horizontal plane and segment 100b is disposed forwardly of and equidistantly between segments 100a and 100c. While such a modified kidney-shaped cage 100 configuration is preferred for use in the anterior portion of the vertebral body, a conventional kidney-shaped configuration also could be employed. As seen in FIG. 5, the modified kidney-shaped cage 100 is substantially identical in all respects to cage 10 except for its shape and, in its preferred configuration, the absence of a transverse wall and a slightly different tool opening configuration. The openings formed at 45 degrees with respect to the transverse wall also may be omitted in cage 100. It is to be understood, however, the different tool opening configurations and positionings could be employed in each of the cages embodying the present invention.

When used in certain applications such as on the sides of the vertebral body, the cage of the present invention can be of a smaller oval-shaped configuration as seen in FIG. 6. As seen therein, the oval-shaped cage 200 is of the same configuration as cages 10 and 100 except for its shape, slightly smaller size and the fact that the oval-shaped cage 200, like cage 100, does not employ a transverse interior wall and has fewer tool engaging openings 230. For stacked applications, cage 200 is shown as having only two indexing apertures 228 disposed at its extended ends. Because the embodiment of cage 200 shown in the drawings does not include a transverse wall like wall 18 of the first embodiment, the slots 237 for receiving the projections 250 on the resilient tabs 246 and 248 on the spacing element 238 used with cage 200 may be positioned on the opposed interior side walls of cage 200. Only one such slot is visible in FIG. 6.

Figure 7:
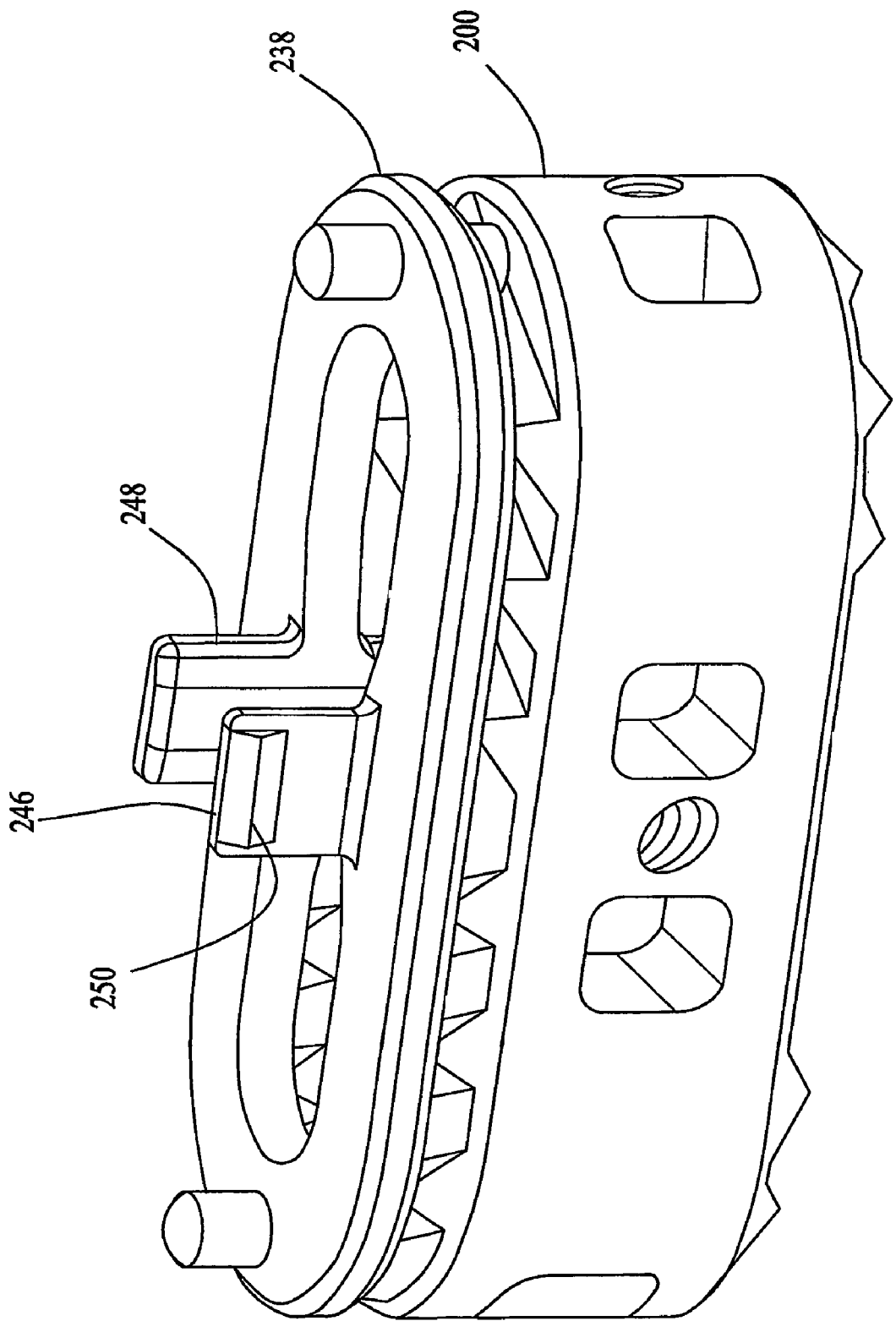
FIG. 7 is a perspective view of the oval-shaped cage of FIG. 6 with a spacing element attached thereto.

The spacing elements 238 used with cages 200 are modified accordingly such that the cage engaging projections 250 extend outwardly from tabs 246 (only one being seen in FIG. 7), not inwardly as in the spacing elements 38. Spacing elements 238 are used with two or more cages 200 of different elevations to form a stack of a desired elevation just as cages 10 and spacing elements 38 are employed in the first embodiment. As seen in FIG. 7, the oval shape of the spacing elements again conforms to the cage configuration. Similarly, when used with a cage 100 having the modified kidney-shaped configuration of FIG. 5, the spacing element also would have a modified kidney-shape. While not shown, the spacing element used with cages 100 also would be configured to define the same or similar indexing and attachment means as shown with respect to spacing elements 238.

It is to be understood that other changes and modifications also could be employed in the present invention without departing from the spirit and scope thereof. For example, a conventional kidney-shaped cage 400 (see FIG. 10) could be employed in lieu of the modified kidney-shape of cage 100. Cage 400, like cage 10, could include a transverse wall portion 418. Accordingly, a spacer element employed with cage 400 would be kidney-shaped and preferably index and attach using generally the same indexing pin and locking tab configuration employed in the spacing elements 38 used with cages 10.

What is claimed is:

1. A cage assembly adapted to be implanted in a spinal column for treating degenerative or ruptured discs and replacing damaged vertebral bodies, said assembly comprising a rigid cage formed in an annular configuration of a biologically inert material, said cage having opposed upper and lower surfaces extending about perimeter portions thereof;

an annular side wall extending between said surfaces;

a plurality of raised ridges projecting outwardly from each one of said upper and lower surfaces for engaging the spinal column and securing the assembly therein and disposed at offset angles with respect to each other;

wherein at least one of said surfaces of said cage defines a plurality of indexing members thereon and wherein said cage assembly includes at least one spacing element adapted to be secured to said one cage for the stacked attachment of said cage with a second cage, said indexing members cooperating with portions of said spacing element for axially aligning said spacing element with said one cage, said spacing element is configured to have flat upper and lower surfaces that do not include said raised ridges and is further configured to be spaced apart from respective upper and lower surfaces of said cage and said second cage when said cage assembly is implanted into the spinal column;

a plurality of spaced apertures in said side wall for use in positioning said cage in the spinal column in a desired angular orientation; and a pair of axially aligned openings extending axially through said cage, said openings being adapted to be packed with bone graft material to expedite the fusion of the cage assembly in the spinal column.

2. The cage assembly of claim 1 wherein the ridges on at least a portion of one of said surfaces are angularly offset with respect to the ridges on at least a portion of the other of said surfaces whereby sliding movement of the cage assembly with respect to the spinal column is inhibited.

3. The cage assembly of claim 1 wherein the spacing element has an axial dimension which is less than an axial dimension of the annular side wall of the cage assembly.

4. A cage assembly adapted to be implanted in a spinal column for treating degenerative or ruptured discs and replacing damaged vertebral bodies, said assembly comprising at least one rigid cage formed in an annular configuration of a biologically inert material, said cage having opposed upper and lower surfaces extending about perimeter portions thereof;

an annular side wall extending between said surfaces, a transverse inner wall extending across said cage;

a plurality of raised ridges projecting outwardly from each of said upper and lower surfaces for engaging the spinal column and securing the assembly therein and disposed at offset angles with respect to each other;

wherein at least one of said surfaces of said cage defines a plurality of indexing members thereon and wherein said cage assembly includes at least one spacing element adapted to be secured to said one cage for the stacked attachment of said cage with a second cage, said indexing members cooperating with portions of said spacing element for axially aligning said spacing element with said one cage, said spacing element is configured to have flat upper and lower surfaces that do not include said raised ridges and is further configured to be spaced apart from respective upper and lower surfaces of said cage and said second cage when said cage assembly is implanted into the spinal column;

a plurality of spaced apertures in said side wall for use in positioning said cage in the spinal column in a desired angular orientation; and a pair of axially aligned openings extending axially through said cage, said openings being adapted to be packed with bone graft material to expedite the fusion of the cage assembly in the spinal column.

5. The cage assembly of claim 4 wherein said spacing element comprising an annular ring portion, a transverse portion extending thereacross, a first plurality of indexing members adapted to engage said indexing members on said one cage for axially aligning said spacing element with said one cage such that said ring and transverse portions of said spacing element are disposed over and axially aligned with said upper surface and said transverse inner wall of said one cage and a second plurality of indexing members for engaging and axially aligning a second cage with said one cage.

6. The cage assembly of claim 5 wherein said spacing element additionally comprises a first pair of resilient locking members carried by said transverse portion thereof for engaging said transverse wall portion of said one cage, rigidly securing said spacing element to said one cage, and a second pair of resilient locking members carried by said transverse portion of said spacing element and extending in an opposed direction from said first pair of locking members for rigidly securing said spacing element to a second cage.

7. The cage assembly of claim 4 including a second cage having substantially the same configuration as said one cage and said spacing element adapted to be secured to and between said one cage and said second cage for forming a rigid stacked cage configuration of a predetermined axial length, said cages each defining indexing members thereon adapted to cooperate with said spacing element so as to axially align said one cage with said second cage and including attachment members carried by said spacing element for engaging said cages so as to define a rigid securement of said cages to said spacing element.

8. The cage assembly of claim 7 wherein said spacing element comprises an annular ring portion and a transverse portion extending thereacross said portions of said spacing element being configured such that upon said spacing element being secured to and between said cages, said assembly defines a substantially continuous annular configuration.

9. The cage assembly of claim 7 wherein said continuous annular configuration is substantially half-moon-shaped.

10. The cage assembly of claim 7 wherein said continuous annular configuration is substantially kidney-shaped.

11. The cage assembly of claim 4 wherein the ridges on at least a portion of one of said surfaces are angularly offset with respect to the ridges on at least a portion of the other of said surfaces whereby sliding movement of the cage assembly with respect to the spinal column is inhibited.

12. The cage assembly of claim 4 wherein said indexing members on said one cage comprise a plurality of apertures in said upper surface of said one cage and wherein said spacing element defines a first plurality of indexing pins adapted to be received in said apertures in said one cage for axially aligning said spacing element with said one cage.

13. The cage assembly of claim 12 wherein said spacing element defines a second plurality of indexing pins axially aligned with and projecting in an opposed axial direction from said spacing element as said first plurality of indexing pins for the securement of said one cage with a second cage.

14. The cage assembly of claim 4 wherein said annular side wall of said one cage assembly and said spacing element are substantially half-moon-shaped so as to generally conform with cross-sectional configuration of the portion of the spinal column within which said cage assembly is to be inserted.

15. The cage assembly of claim 4 wherein said annular side wall of said one cage assembly and said spacing element are substantially kidney-shaped so as to generally conform with cross-sectional configuration of the portion of the spinal column within which said cage assembly is to be inserted.

16. The cage assembly of claim 4 wherein the spacing element has an axial dimension which is less than an axial dimension of the annular side wall of the cage assembly.

17. A cage assembly adapted to be implanted in a spinal column for treating degenerative or ruptured discs and replacing damaged vertebral bodies, said assembly comprising
at least one rigid cage formed in an annular configuration of a biologically inert material, said cage having opposed upper and lower surfaces extending about perimeter portions thereof;
an annular side wall extending between said surfaces;
a plurality of raised ridges projecting outwardly from each one of said upper and lower surfaces for engaging the spinal column and securing the assembly therein and disposed at offset angles with respect to each other;
wherein at least one of said surfaces of said cage defines a plurality of indexing members thereon and wherein said cage assembly includes at least one spacing element adapted to be secured to said one cage for the stacked attachment of said cage with a second cage, said indexing members cooperating with portions of said spacing element for axially aligning said spacing element with said one cage, said spacing element is configured to have flat upper and lower surfaces that do not include said raised ridges and is further configured to be spaced apart from respective upper and lower surfaces of said cage and said second cage when said cage assembly is implanted into the spinal column;
a plurality of spaced apertures in said side wall for use in positioning said cage in the spinal column in a desired angular orientation; and
a pair of axially aligned openings extending axially through said cage, said openings being adapted to be packed with bone graft material to expedite the fusion of the cage assembly in the spinal column.

18. The cage assembly of claim 17 wherein said spacing element comprising an annular ring portion, a first plurality of indexing members adapted to engage said indexing members on said one cage for axially aligning said spacing element with said one cage such that said ring portion of said spacing element is disposed over and axially aligned with said upper surface of said one cage and a second plurality of indexing members for engaging and axially aligning a second cage with said one cage.

19. The cage assembly of claim 17 including a second cage having substantially the same configuration as said one cage and said spacing element adapted to be secured to and between said one cage and said second cage for forming a rigid stacked cage configuration of a predetermined axial length, said cages each defining indexing members thereon adapted to cooperate with said spacing element so as to axially align said one cage with said second cage and including attachment members carried by said spacing element for engaging said cages so as to define a rigid securement of said cages to said spacing element.

20. The cage assembly of claim 17 wherein the ridges on at least a portion of one of said surfaces are angularly offset with respect to the ridges on at least a portion of the other of said surfaces whereby sliding movement of the cage assembly with respect to the spinal column is inhibited.

21. The cage assembly of claim 17 wherein said annular configuration defines a modified kidney-shape.

22. The cage assembly of claim 17 wherein said annular configuration defines an oval.

23. The cage assembly of claim 17 wherein said indexing members on said one cage comprise a plurality of apertures in said upper surface of said one cage and wherein said spacing element defines a first plurality of indexing pins adapted to be received in said apertures in said one cage for axially aligning said spacing element with said one cage.

24. The cage assembly of claim 17 wherein said annular side wall of said one cage assembly and said spacing element are substantially oval-shaped so as to generally conform with cross-sectional configuration of the portion of the spinal column within which said cage assembly is to be inserted.

25. The cage assembly of claim 17 wherein the spacing element has an axial dimension which is less than an axial dimension of the annular side wall of the cage assembly.

* * * * *